(12) United States Patent
Jacobelli et al.

(10) Patent No.: US 6,365,585 B1
(45) Date of Patent: Apr. 2, 2002

(54) PHOSPHODIESTERASE IV-INHIBITING DIAZEPINOINDOLES

(75) Inventors: Henry Jacobelli, Paray-Vieille-Poste; Christine Julien-Larose, Colombes; Sylvie Marc, Gif-sur-Yvette, all of (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/556,000
(22) PCT Filed: Mar. 26, 1999
(86) PCT No.: PCT/EP99/02336
§ 371 Date: Jun. 7, 2000
§ 102(e) Date: Jun. 7, 2000
(87) PCT Pub. No.: WO99/50270
PCT Pub. Date: Oct. 7, 1999

(30) Foreign Application Priority Data

Mar. 27, 1998 (FR) .............................. 98 03851

(51) Int. Cl.[7] ...................... C07D 487/06; A61K 31/55
(52) U.S. Cl. ........................ 514/220; 540/496
(58) Field of Search ........................... 514/220; 540/496

(56) References Cited

U.S. PATENT DOCUMENTS 4,929,614 A * 5/1990 Calvet et al. ............... 514/214
4,981,847 A * 1/1991 Sato et al. ................... 514/211
5,852,190 A * 12/1998 Pascal et al. ................ 540/496

FOREIGN PATENT DOCUMENTS

| WO | WO 96/06617 | * 3/1996 |
| WO | 96/11690 | 4/1996 |

* cited by examiner

Primary Examiner—Bruck Kifle
(74) Attorney, Agent, or Firm—Charles W. Ashbrook; Claude F. Purchase, Jr.

(57) ABSTRACT

Metabolites of the products of formula (I)

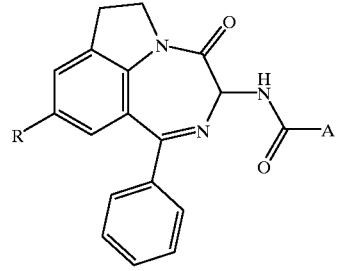

in which A and R are as defined in the description, which are phosphodiesterase 4 inhibitors.

22 Claims, No Drawings

PHOSPHODIESTERASE IV-INHIBITING DIAZEPINOINDOLES

The subject of the invention is metabolites of the products of formula I, and compounds of formula II and formula III below.

1. Field of the Invention

The present invention relates to [1,4]diazepino-[6,7,1-hi] indoles, and to those for the preparation of medicaments that enable treatment of affections which are amenable to therapy by a phosphodiesterase IV inhibitor. These medicaments are useful, in particular, as anti-inflammatories, anti-allergics, bronchodilators or anti-asthmatics and are devoid of digestive or cardiac side-effects.

2. Technological Background of the Invention

WO-A-9611690 describes [1,4]diazepino[6,7,1-hi] indoles, including in particular (3R)-N-(9-methyl-4-oxo-1-phenyl-3,4,6,7-tetrahydro[1,4]diazepino[6,7,1-hi]indol-3-yl)isonicotinamide. (which will be abbreviated to MPTDI in the text which follows).

SUMMARY OF THE INVENTION

The subject of the invention is metabolites of the products of formula I and of the products of formula II or III below.

DETAILED DESCRIPTION OF THE INVENTION

In a first aspect, the invention relates to the metabolites of the products of formula (I):

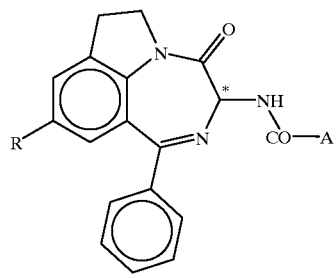

(I)

in which:

R is a lower alkyl or alkoxy;

A is aryl, nitrogen-containing heteroaryl or sulphur-containing heteroaryl, each optionally substituted with one to three groups independently chosen from halogen, lower alkyl, haloalkyl, lower alkoxy, hydroxyl, acetoxy, amino, t-butoxycarbonylamino, cycloalkylcarbonylamino or acetamido; of their racemic forms, of their isomers having a configuration which is determined by the carbon at the 3-position of the diazepinoindol-4-one ring, and of their pharmacologically acceptable salts.

Preferably, R is a methyl group.

Preferably, the asymmetric carbon has the R configuration.

Preferably, the product of formula I is the product N-(9-methyl-4-oxo-1-phenyl-3,4,6,7-tetrahydro-[1,4]diazepino[6,7,1-hi]indol-3-yl)isonicotinamide, advantageously the configuration is 3R.

This term <<metabolite>> covers these products derived from biodegradation by a mammal, in particular humans, of the said products of formula I.

The, preferred metabolites are those which are oxidized and/or hydroxylated, on the substituents and/or the rings and/or heterocycles.

In particular, the invention relates to the metabolites corresponding to the derivatives which are hydroxylated on the pyrrolidine or 1-phenylbenzodiazepine ring.

Advantageously, the products are those in which A is pyridyl, optionally N-oxidized.

In a second aspect, the invention relates to the diazepinoindoles of formula (II)

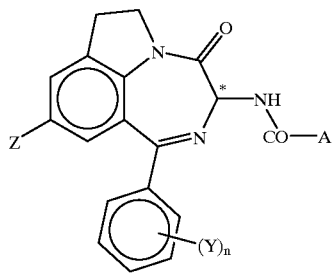

in which:

Z is a lower alkyl or alkoxy;

A is aryl, nitrogen-containing heteroaryl or sulphur-containing heteroaryl, each optionally substituted with one to three groups independently chosen from halogen, lower alkyl, haloalkyl, lower alkoxy, hydroxyl, acetoxy, amino, t-butoxycarbonylamino, cycloalkylcarbonylamino or acetamido, the N-oxide or S-oxide forms;

Y is hydroxyl or lower alkoxy;

n is 1 or 2.

of their racemic forms, of their isomers having a configuration which is determined by the carbon at the 3-position of the diazepinoindol-4-one ring, and of their pharmacologically acceptable salts.

Preferably, Y is hydroxyl or methoxy.

The phenyl is preferably substituted at the para-position, advantageously with a hydroxyl.

Advantageously, the products are those in which A is pyridyl, optionally N-oxidized.

Among the diazepinoindoles of formula (II), those in which the asymmetric carbon atom at the alpha-position with respect to the carbonyl of the diazepine ring has the absolute configuration (R), are preferred.

Examples of such products are reproduced below:

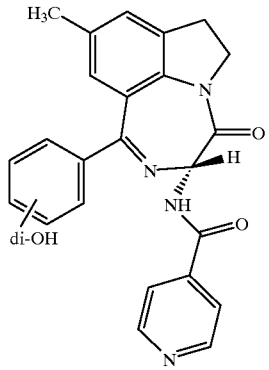

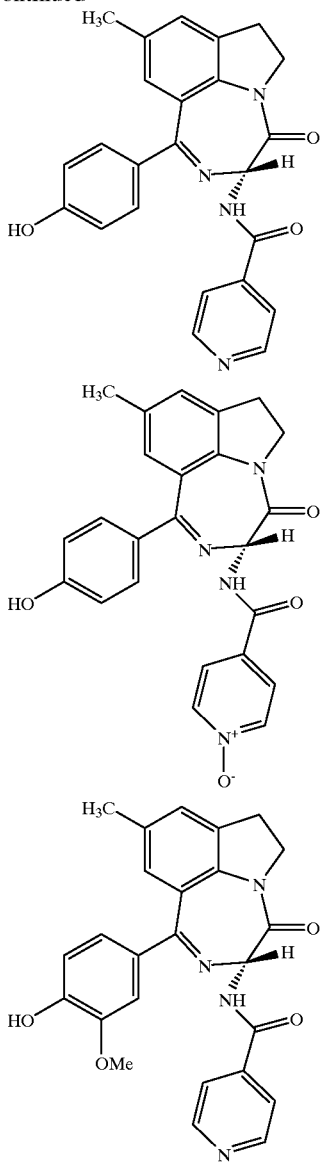

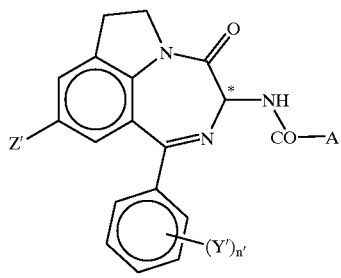

In a third aspect, the invention relates to the diazepinoindoles of formula (III)

in which:
Z' is hydroxymethyl, formyl, carboxylic acid in its free form, salified, esterified or amidated, hydroxymethyl whose hydroxyl group is esterified;
A' is aryl, nitrogen-containing heteroaryl or sulphur-containing heteroaryl, each optionally substituted with one to three groups independently chosen from halogen, lower alkyl, haloalkyl, lower alkoxy, hydroxyl, acetoxy, amino, t-butoxycarbonylamino, cycloalkylcarbonylamino or acetamido, the N-oxide or S-oxide forms;

Y' is hydroxyl or lower alkoxy;

n' is 0, 1 or 2.

of their racemic forms, of their isomers having a configuration which is determined by the carbon at the 3-position of the diazepinoindol-4-one ring, and of their pharmacologically acceptable salts.

Preferably, Z' is chosen from the group consisting of hydroxymethyl; formyl; COOH; CONH$_2$, COOD where D is a lower alkyl, optionally hydroxylated; —CH$_2$—O—C(O)—E where E is a lower alkyl, an aryl, cycloalkyl, or pyridyl.

Preferably, Y' is hydroxyl or methoxy.

The phenyl is preferably substituted at the para-position, advantageously with a hydroxyl. Among the diazepinoindoles of formula (III), those in which the asymmetric carbon atom at the alpha-position with respect to the carbonyl of the diazepine ring has the absolute configuration (R), are preferred.

Advantageously, the products are those in which A' is pyridyl, optionally N-oxidized.

Examples of such products are reproduced below:

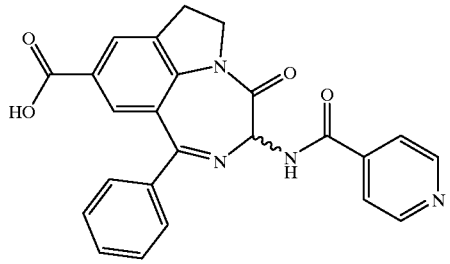

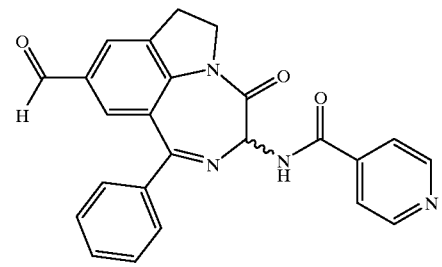

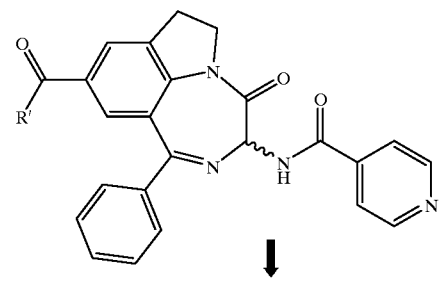

R' = NH2
R' = —O—CH2—CH2—OH

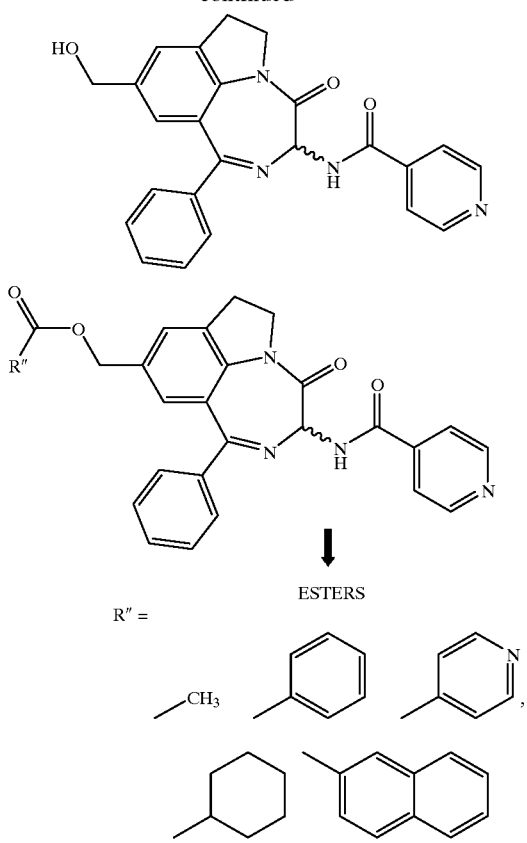

ESTERS

In the foregoing as well as hereinafter:

aryl is understood to mean a phenyl or naphthyl group;

nitrogen- or sulphur-containing heteroaryl is understood to mean an unsaturated monocyclic or polycyclic group containing at least one nitrogen or sulphur atom, respectively, and preferably these heterocycles may be four- to seven-membered heteromonocyclic groups containing from 1 to 4 heteroatoms, or unsaturated fused heterocyclic groups containing from 1 to 4 heteroatom; the heteroaryl group may be methylated or ethylated on a positively charged nitrogen;

halogen is understood to mean fluorine, chlorine, bromine or iodine;

lower alkyl is understood to mean linear or branched alkyl groups containing from one to four carbon atoms;

cycloalkyl is understood to mean cyclopropyl, cyclobutyl and cyclopentyl groups;

lower alkoxy is understood to mean an O-alkyl group in which the alkyl group is a lower alkyl as defined above;

haloalkyl is understood to mean a mono-, di- or trihaloalkyl containing from 1 to 4 carbon atoms.

A review of salts which are acceptable in pharmacy will be found in J. Pharm. Sci., 1977, 66, 1–19. However, pharmacologically acceptable salt of a compound of formula (I) possessing a basic portion is understood to mean the addition salts of the compounds of formula (I) which are formed from nontoxic inorganic or organic acids such as, for example, the salts of hydrobromic, hydrochloric, sulphuric, sulphamic, phosphoric, nitric, acetic, propionic, succinic, glycolic, stearic, lactic, malic, tartaric, citric, mucic, ascorbic, pamoic, maleic, hydroxymaleic, phenylacetic, glutamic, benzoic, salicylic, sulphanilic, acetoxybenzoic, fumaric, toluenesulphonic, ethanedisulphonic, oxalic, isethionic and the like, acids. The various quaternary ammonium salts of the derivatives (I) are also included in this category of the compounds of the invention. And pharmacologically acceptable salt of a compound of formula (I) possessing an acidic portion is understood to mean the commonplace salts of the compounds of formula (I) which are formed from nontoxic inorganic or organic bases such as, for example, alkali metal and alkaline-earth metal hydroxides (lithium, sodium, potassium, magnesium and calcium hydroxides), amines (dibenzylethylenediamine, trimethylamine, piperidine, pyrrolidine, benzylamine and the like) or alternatively quaternary ammonium hydroxides such as tetramethylammonium hydroxide.

The invention also relates to the above products as a medicament, and in particular for combating inflammatory diseases, allergic diseases and bronchoconstriction, or which is useful in the treatment of asthma, characterized in that it comprises a diazepinoindole according to the invention, in a pharmaceutical dosage form which is suited to the disease to be treated. The invention also relates to the use of the above products for the preparation of the above-mentioned medicaments.

The compounds according to the invention may be synthesized by conventional routes from compounds of formula I as described in Application WO-A-9611690, by biological routes or by chemical synthesis.

The following examples illustrate the use of the products of the invention without however limiting it.

EXPERIMENTAL PART

Metabolism In Vitro of MPTDI in Humans

The profile and the identification of the metabolites of MPTDI were obtained after incubation of the product with human hepatic microsomes. The results were compared with those obtained on rat hepatic microsomes. The metabolic profiles obtained by HPLC coupled to a mass spectrometer in these two species are represented in FIG. 1. In some cases, the mass spectra obtained were compared with those of reference substances synthesized by the chemical route. It is deduced therefrom that the profiles obtained on human and rat microsomes are similar: Table 1 collates the measured proportions of the metabolites for these two species.

TABLE 1

Proportions (%) of the metabolites obtained on human and rat hepatic microsomes

| Compound | Human microsomes | Rat microsomes |
|---|---|---|
| MPTDI | 79 | 38.2 |
| OH on 9-CH3 | 4.2 | 24.3 |
| OH on pyrrolidine | 7.4 | 13 |
| OH on Bdz* | 7.1 | 2.6 |
| N-oxide | 0.7 | 5.1 |
| Other | 1.2 | traces |

Bdz means 1-phenylbenzodiazepine ring

Examples of synthesis of the compounds.

Stage No. 1: N-(9-cyano-4-oxo-1-phenyl-3,4,6,7-tetra-hydro [1,4]diazepino[6,7,1-hi]indol-3-yl) isonicotinamide 30 ml of water, 7 ml of concentrated hydrochloric acid and 10 g (25.2 mmol) of N-(9-amino-4-oxo-1-phenyl-3,4, 6,7-tetrahydro[1,4]diazepino[6,7,1-hi]indol-3-yl)- isonicotinamide are successively introduced into a 250-ml three-necked flask. The orange-red solution obtained is cooled to 0° C. A solution of sodium nitrite (1.83 g, 26.5 mmol) in 5 ml of water is poured therein at a temperature of less than 5° C. The orange-yellow solution is kept stirring for 30 min at 0° C. The reaction mixture is neutralized with about 3 g of $Na_2CO_3$, while maintaining a temperature of less than 5° C.; foams are formed during the neutralization. The liquors are transferred rapidly into a three-necked flask, with stirring, containing a solution of NaC≡N (3.04 g, 62.0 mmol) and of CuC≡N (2.72 g, 30.4 mmol) in 10 ml of water, while maintaining the temperature at 0° C. Foams appear; a few millimetres of ice-cold water are added. The reaction medium is stirred for 30 min at about 0° C. and then extracted with twice 200 ml of $CH_2Cl_2$. The medium is filtered on infusorial earth and the phases are separated after settling out. The organic phase is washed with twice 200 ml of water and then dried over anhydrous $Na_2SO_4$. The solvent is removed under vacuum. The brown foamy residue is purified by rapid chromatography on a silica column, eluting with $CH_2Cl_2$ progressively enriched with MeOH. 5.6 g (13.7 mmol) of product are obtained in the form of a yellow powder.

Yield=54.5%—m.p.=174° C. Analysis conforms for $C_{24}H_{17}O_2N_5$ (0.3 $H_2O$) TLC ($CH_2Cl_2$/MeOH 95/5 v/v): Rf=0.70. $^1$H NMR δ (ppm): 3.15–3.25 (m, 1H); 3.35–3.50 (m, 1H); 4.05 (q, 1H); 4.5 (td, 1H); 5.55 (d, 1H); 7.4–7.6 (m, 5H); 7.7 (s, 1H); 7.95 (d, 2H); 8.0 (s, 1H); 8.75 (d, 2H); 10.05 (d, 1H). IR: 3300, 2200, 1690, 1660, 1610, 1510, 1430, 1280, 1130, 890, 850, 700 cm$^{-1}$.

Stage No. 2: N-(9-aminomethyl-4-oxo-1-phenyl-3, 4,6,7-tetrahydro[1,4]diazepino[6,7,1-hi]indol-3-yl) isonicotinamide A solution of the nitrile obtained in stage No. 1 (5.6 g, 13.7 mmol) in 280 ml of MeOH is introduced into a 500-ml stainless steel autoclave. The apparatus is cooled with a dry ice/acetone bath at about −40° C. 35 ml of liquid ammonia are then added. In parallel, Raney nickel, washed three times with water, is carefully introduced into the reactor, followed by methanol. After hermetically closing the apparatus, it is purged three times with nitrogen and then with hydrogen. The autoclave is placed under a hydrogen pressure of 4 bar and stirred. The internal temperature is raised to 50–55° C. for 3 h. After cooling, the apparatus is purged under vacuum and under nitrogen. The catalyst is removed by filtration on infusorial earth and washed with MeOH. The filtrate is evaporated under vacuum. A foamy residue of 5.3 g is obtained and purified by rapid chromatography, eluting with $CH_2Cl_2$ progressively enriched with methanol containing 10% ammonium hydroxide. 2.4 g (5.8 mmol) of a beige powder are obtained. Yield=42%

The product is analysed in the form of a dihydrochloride prepared with an approximately 3.5 N hydrochloric ether and crystallized from an isopropanol/methanol mixture. m.p. >270° C.—Analysis conforms for $C_{24}H_{21}N_5O_2$. 2HCl (0.5 $H_2O$) TLC ($CH_2Cl_2$/MeOH containing 10% $NH_4OH$ 90/10 v/v): Rf=0.50. $^1$H NMR (base) δ (ppm): 1.80 (m, 2H); 3–3.1 (m, 1H); 3.2–3.3 (m, 1H); 3.8 (s, 2H); 3.9–4.00 (m, 1H); 4.6–7.7 (m, 1H); 5.5 (d, 1H); 7.1 (s, 1H); 7.3–7.5 (m, 6H); 7.7 (d, 2H); 8.1 (d, 1H); 8.7 (d, 2H). IR (di-HCl) : 3300, 2800, 2600, 1680, 1650, 1600, 1540, 1440, 1280, 1230, 1100, 1000, 830, 760, 700 cm$^{-1}$.

Stage No. 3: N-(9-hydroxymethyl-4-oxo-1-phenyl-3,4,6,7-tetrahydro[1,4]diazepino[6,7,1-hi]indol-3-yl) isonicotinamide 2.4 g (5.8 mmol) of the product obtained in stage No. 2 dissolved in 21.2 ml of 10% acetic acid (w/v) are cooled to 0° C. with a brine bath; a solution of sodium nitrite (1.25 g, 18 mmol) in 7 ml of water is slowly added. The mixture is stirred for 2 h at 0° C. After alkalinizing with 14 ml of 4 N sodium hydroxide, it is extracted with twice 50 ml of $CH_2Cl_2$. The organic phase is dried over $Na_2SO_4$ and then evaporated under vacuum. The residue obtained is purified by rapid chromatography, eluting with $CH_2Cl_2$ progressively enriched with MeOH. The fractions of interest are concentrated under vacuum. The product is crystallized from 18 ml of $CH_2Cl_2$. The precipitate is filtered off and then dried under vacuum. 0.9 g is obtained. Yield: 38%—White powder m.p.=260° C.—Analysis conforms for $C_{24}H_{20}N_4O_3$ (0.1 $CH_3OH$), (0.1 $H_2O$)—TLC ($CH_2Cl_2$/MeOH 90/10 v/v): Rf=0.80.

$^1$H NMR δ (ppm): 3.1 (m, 1H); 3.3 (m, 1H); 3.9 (q, 1H); 4.5 (m, 3H); 5.2 (t, 1H); 5.4 (d, 1H); 7.2 (s, 1H); 7.4–7.6 (m, 6H); 8.0 (d, 2H); 8.80 (d, 2H); 10.0 (d, 1H) IR: 3400, 3300, 3050, 2850, 1680, 1660, 1530, 1480, 1440, 1400, 1360, 1290, 1220, 1190, 1120, 1060, 900, 860, 780, 760, 700 cm$^{-1}$.

Separation of the Optical Isomers of N-(9-hydroxymethyl-4-oxo-1-phenyl-3,4,6,7-tetrahydro-[1,4]diazepino[6,7,1-hi]indol-3-yl)isonicotinamide This was carried out on a Merck high-performance liquid chromatography system composed of a pump and a UV detector, provided with a fraction collector. The chiral column used is of the Chiralcel OJ type, 20×250 mm, 10 μm particles, thermostated at 35° C. The injections are twenty times 5 ml of an ethanolic solution at 7 mg/ml, by means of a Rheodyne valve. The operating conditions are the following: solvent: hexane/ethanol 75/25 (v/v), flow rate: 6 ml/min, pressure: 12 bar, UV detection: 254 nm. The fractions containing each isomer are collected and then the solvent removed under vacuum.

1st Isomer: Retention Time=28–38 min.

Beige crystallized residue, purified by dissolution in a $CH_2Cl_2$/MeOH mixture, and then precipitation by addition of hexane. 0.190 g of a beige powder is obtained. m.p.=251° C.

Analysis conforms for $C_{24}H_{20}N_4O_3$ (0.5 $CH_3OH$)—TLC ($CH_2Cl_2$/MeOH 90/10 v/v): Rf=0.80. Chiral HPLC (Chiralcel OJ column, 250×4.6 mm, 10 μm particles, thermostated at 35° C., solvent: hexane/ethanol 70/30 (v/v), flow rate: 1.2 ml/min, UV detection at 254 nm): retention time=7.8 min at 100% optical purity.

$^1$H NMR δ (ppm): 3.1 (m, 1H); 3.3 (m, 1H); 3.9 (q, 1H); 4.5 (m, 3H); 5.2 (t, 1H); 5.4 (d, 1H); 7.2 (s, 1H); 7.4–7.6 (m, 6H); 8.0 (d, 2H); 8.80 (d, 2H); 10.0 (d, 1H) IR: 3380, 2800, 1690, 1650, 1530, 1425, 1360, 1180, 1120, 1060, 900, 840, 780, 690 cm$^{-1}$.

2nd Isomer: Retention Time=41–54 min.

In the same manner, 0.220 g of a beige powder is obtained. m.p.=253° C.—Analysis conforms for $C_{24}H_{20}N_4O_3$ (0.5 $CH_3OH$) TLC ($CH_2Cl_2$/MeOH 90/10 v/v): Rf=0.80. Chiral HPLC (Chiralcel OJ column, 250×4.6 mm, 10 μm particles, thermostated at 35° C., solvent: hexane/ethanol 70/30 (v/v), flow rate: 1.2 ml/min, UV detection at 254 nm): retention time=10.8 min at 99% optical purity.

$^1$H NMR δ (ppm): 3.1 (m, 1H); 3.3 (m, 1H); 3.9 (q, 1H); 4.5 (m, 3H); 5.2 (t, 1H); 5.4 (d, 1H); 7.2 (s, 1H); 7.4–7.6 (m, 6H); 8.0 (d, 2H); 8.80 (d, 2H); 10.0 (d, 1H) IR: 3380, 2800, 1690, 1650, 1530, 1425, 1360, 1180, 1120, 1060, 900, 840, 780, 690 cm$^{-1}$.

N-(9-formyl-4-oxo-1-phenyl-3,4,6,7-tetrahydro-[1,4] diazepino[6,7,1-hi]indol-3-yl)-isonicotinamide 0.100 g (0.24 mmol) of N-(9-hydroxymethyl-4-oxo-1-phenyl-3,4,6,7-tetrahydro-[1,4]diazepino[6,7,1-hi]indol-3- yl)-isonicotinamide and 20 ml of $CH_2Cl_2$ are introduced successively into a 50-ml one-necked flask. The mixture is stirred and 0.200 g (0.93 mmol) of pyridinium chlorochromate are added. The suspension is stirred for 1 h at 20–25° C. The purification is carried out directly on the reaction mixture by rapid chromatography on a silica column, eluting with $CH_2Cl_2$ enriched with MeOH. The residue obtained after removal of the solvent is concreted in a few millilitres of ether. 0.022 g (0.054 mmol) of a beige powder is obtained.—TLC ($CH_2Cl_2$/MeOH 95/5 v/v): Rf=0.50.

$^1$H NMR δ (ppm): 3.07–3.18 (m, 1H); 3.2–3.35 (m, 1H); 3.9–4.0 (q, 1H); 4.5–4.6 (t, 1H); 5.50 (d, 1H); 7.2–7.3 (m, 2H); 7.3–7.4 (m, 3H); 7.6 (s, 1H); 7.7 (d, 2H); 7.85 (s, 1H); 8.3 (d, 1H); 8.65 (d, 2H); 9.75 (s, 1H)

4-Oxo-1-phenyl-3[(pyridine-4-carbonyl)amino]-3,4, 6,7-tetrahydro-[1,4]diazepino[6,7,1-hi]indole-9-carboxylic Acid 2-Hydroxyethyl Ester 0.6 g (1.5 mmol) of N-(9-cyano-4-oxo-1-phenyl-3,4,6,7-tetrahydro-[1,4]diazepino[6,7,1-hi]indol-3-yl) isonicotinamide is introduced into a three-necked flask followed by 110 ml of ethylene glycol; the mixture is stirred and 1.5 ml (4.5 mmol) of 3 N sodium hydroxide are added. The medium is stirred for 4 days at 20–25° C., is then poured over 400 ml of water and ice, is acidified with 1 N hydrochloric acid and is then extracted with twice 200 ml of $CH_2Cl_2$. The organic phases are dried over $Na_2SO_4$ and the solvent removed by concentrating under vacuum. The residue is purified by rapid chromatography on silica, eluting with $CH_2Cl_2$ enriched with MeOH. 0.13 g of product is obtained. Yield=18%.—TLC ($CH_2Cl_2$/MeOH 95/5 v/v): Rf=0.36

$^1$H NMR δ (ppm): 2.45 (OH); 3.05–3.2 (m, 1H); 3.25–3.4 (m, 1H); 3.85 (t, 2H); 4.0 (q, 1H); 4.35–4.5 (m, 2H); 4.6 (td, 1H); 5.55 (d, 1H); 7.25–7.35 (m, 2H); 7.4–7.5 (m, 3H); 7.75 (d, 2H); 7.9 (s, 1H); 8.0 (s, 1H); 8.1 (d, 1H); 8.7 (d, 2H)

Isdnicotinic Acid 4-oxo-1-phenyl-3[(pyridine-4-carbonyl)-amino]-3,4,6,7-tetrahydro-[1,4]diazepino [6,7,1-hi]indol-9-ylmethyl Ester 0.1 g (0.24 mmol) of N-(9-hydroxymethyl-4-oxo-1-phenyl-3,4,6,7-tetrahydro-[1,4]diazepino[6,7,1-hi]indol-3-yl)isonicotinamide in 10 ml of anhydrous $CH_2Cl_2$ is introduced into a three-necked flask under an inert atmosphere and protected from moisture, it is stirred and 0.0475 g (0.27 mmol) of isonicotinoyl chloride hydrochloride is introduced at a temperature close to 15° C. The suspension is stirred for 10 min at this temperature and then heated under reflux for 1.5 h. 10 ml of $CH_2Cl_2$ are added and the mixture is treated with a dilute $NaHCO_3$ solution. The organic phase is decanted off and the solvent is removed by concentrating under vacuum. The 0.1 g residue is purified by rapid chromatography on silica, eluting with $CH_2Cl_2$ enriched with MeOH. 0.028 g of product is obtained. Yield=22%

TLC ($CH_2Cl_2$/MeOH 95/5 v/v): Rf=0.57. $^1$H NMR δ (ppm): 3.0–3.2 (d, 2H); 3.3–3.45 (m, 1H); 4.0 (q, 1H); 4.65 (td, 1H); 5.3 (d, 2H); 5.55 (d, 1H); 7.25–7.35 (m, 3H); 7.4–7.55 (m, 4H); 7.7 (d, 2H); 7.75 (d, 2H); 8.0 (d, 1H); 8.7 (d, 2H); 8.75 (d, 2H)

Benzoic Acid 4-Oxo-1-phenyl-3[(pyridine-4-carbonyl)amino]-3,4,6,7-tetrahydro-[1,4]diazepino [6,7,1-hi]indol-9-ylmethyl Ester The title compound is prepared in a similar manner by the above process, but using 10 equivalents of benzoyl chloride and maintaining the reflux for 4.5 h. After treatment and purification, 0.020 g of product is obtained.

TLC ($CH_2Cl_2$/MeOH 95/5 v/v): Rf=0.61. $^1$H NMR δ (ppm): 3.05–3.2 (m, 1H); 3.3–3.45 (m, 1H); 4.05 (q, 1H); 4.7 (td, 1H); 5.35 (d, 2H); 5.65 (d, 1H); 7.3–7.5 (m, 6H); 7.5–7.65 (m, 4H); 7.8 (d, 2H); 8.05 (d, 2H); 8.2 (d, 1H); 8.8 (d, 2H)

Cyclohexanecarboxylic Acid 4-Oxo-1-phenyl-3 [(pyridine-4-carbonyl)amino]-3,4,6,7-tetrahydro-[1, 4]diazepino[6,7, 1-hi]indol-9-ylmethyl Ester The title compound is prepared in a similar manner by the above process, but using 2.3 equivalents of cyclohexanecarboxylic acid chloride and maintaining the reflux for 2.5 h. After treatment and purification, 0.020 g of product is obtained.

TLC ($CH_2Cl_2$/MeOH 95/5 v/v): Rf=0.40. $^1$H NMR δ (ppm): 1.1–1.9 (m, 10H); 2.15–2.3 (m, 1H); 3.0–3.15 (m, 1H); 3.25–3.4 (m, 1H); 3.95 (q, 1H); 4.6 (td, 1H); 5.0 (d, 2H); 5.55 (d, 1H); 7.15 (s, 1H); 7.25–7.5 (m, 6H); 7.75 (d, 2H); 8.1 (d, 1H); 8.75 (d, 2H).

Acetic Acid 4-Oxo-1-phenyl-3[(pyridine-4-carbonyl)amino]-3,4,6,7-tetrahydro-[1,4]diazepino [6,7,1-hi]indol-9-ylmethyl Ester The title compound is prepared in a similar manner by the above process, but using 3 equivalents of acetyl chloride and maintaining the reflux for 3 h. After treatment and purification, 0.020 g of product is obtained.

TLC ($CH_2Cl_2$/MeOH 95/5 v/v): Rf=0.37. $^1$H NMR δ (ppm): 2.0 (s, 3H); 3.05–3.15 (m, 1H); 3.25–3.40 (m, 1H); 3.95 (q, 1H); 4.6 (td, 1H); 5.0 (d, 2H); 5.5 (d, 1H); 7.2 (s, 1H); 7.25–7.35 (m, 2H); 7.4–7.5 (m, 4H); 7.7 (d, 2H); 8.05 (d, 1H); 8.7 (d, 2H).

2-Naphthyl derivative of the Z group The title compound, 2-naphthyl ester, is prepared in a similar manner by the above process, but using 2-naphthoyl chloride. After treatment and purification, 0.007 g of product is obtained.

TLC ($CH_2Cl_2$/MeOH 95/5 v/v): Rf=0.48. $^1$H NMR δ (ppm): 3.1–3.3 (m, 1H); 3.35–3.5 (m, 1H); 4.05 (q, 1H); 4.6–4.8 (t, 1H); 5.4 (d, 2H); 5.65 (d, 1H); 7.3–7.4 (m, 2H); 7.4–7.45 (m, 2H); 7.5–7.7 (m, 5H); 7.8 (d, 2H); 7.85–7.9 (m, 2H); 7.95 (d, 1H); 8.05–8.15 (m 2H); 8.6 (s, 1H); 8.8 (d, 2H).

N-Oxide Derivative of Pyridyne 2.0 g (5 mmol) of MPTDI and 100 ml of $CH_2Cl_2$ are introduced into a three-necked flask protected from moisture; the solution is stirred and cooled by an ice bath. A solution of 1.9 g (5.5 mmol) of 3-chloroperbenzoic acid in 50 ml of $CH_2Cl_2$ is poured in over 10 min at a temperature close to 2° C. The medium is kept stirring for 2 h at this temperature. The reaction liquors are washed successively with a solution of $Na_2CO_3$ and then with a saturated solution of NaCl. After drying over $Na_2SO_4$, the solvent is removed by distillation under a vacuum of 20 mm Hg at 50° C. The 2.0 g of residue are purified by rapid chromatography on a silica column, eluting with $CH_2Cl_2$ progressively enriched with MeOH. 0.7 g of concreted product is obtained in an ether/ethyl acetate mixture.—Beige powder—m.p.=220° C.

TLC ($CH_2Cl_2$/MeOH 95/5 v/v): Rf=0.35. $^1$H NMR δ (ppm): 2.3 (s, 3H); 3.0–3.1 (m, 1H); 3.2–3.3 (m, 1H); 3.85–3.95 (m, 1H); 4.5–4.6 (m, 1H); 5.45 (d, 1H); 6.95 (s, 1H); 7.25 (s, 1H); 7.3–7.5 (m, 5H); 7.75 (d, 2H); 8.2 (m, 3H)

I.R.: 3400, 1660, 1540, 1480, 1430, 1350, 1240, 1180, 1120, 1020, 850, 700 cm$^{-1}$.

BIOLOGICAL PART

The compounds according to the invention are biologically active, as demonstrated by the tests below carried out on these compounds.

Phosphodiesterase-inhibiting Activity

The capacity of the compounds of formula (I) of the invention to inhibit cyclic nucleotide phosphodiesterases is evaluated by measuring their $IC_{50}$ (concentration necessary for inhibiting 50% of the enzyme activity). In the case of the PDE IV enzymes, this value is compared with the $IC_{50}$ of rolipram, a specific PDE IV inhibitor, by the ratio of the $IC_{50}$ of rolipram to the $IC_{50}$ of the test product with respect to the same enzyme preparation The different types of phosphodiesterases are obtained partially purified on a DEAE-cellulose column from guinea pig trachea and dog aorta according to a method adapted from W. J. Thompson et al., 1979, Advances in Cyclic Nucleotide Research, Vol. 10: 69–92, ed. G. Brooker et al. Raven Press, New York, and from P. J. Silver at al., 1988, Eur. J. Pharmacol. 150: 85–94.

Next, the measurement of the enzymatic activity of different types of PDE, and in particular PDE IV, is carried out according to a method also adapted from W. J. Thompson, Ibedem.

To determine the $IC_{50}$, the enzymatic activity is measured in the presence of the inhibitor within a range of concentrations from 0.1 to 100 $\mu M$.

The results show that the products of the invention generally inhibit the PDE IV enzyme of guinea pig trachea more effectively than rolipram, and in a number of cases are twice to three times as active as rolipram.

Moreover, tests carried out on PDEs of different types, purified from guinea pig trachea or from dog aorta, show that the $IC_{50}$ values obtained with the products of the invention with respect to PDEs of type III and of type I and V are much higher than those measured for the type IV PDEs.

These results are evidence of a potent and selective inhibitory activity for the products of the invention with respect to the PDE IV enzymes.

Anti-inflammatory and Anti-allergic Activity in vivo

The effects of the product of the invention were studied in guinea pigs in a model of eosinophil infiltration induced by an antigenic stimulation or by exposure to a PAF spray according to a methodology described by Lagente V. et al., (1994) Br. J. Pharmacol. 112, 83P.

The administration of products of the Examples (1–30 mg/kg p.o.) significantly decreases the number of eosinophils in the bronchoalveolar lavage fluid.

The administration of products of the invention also decreases the in flammatory responses induced by intratracheal instillation of IL-5 in guinea pigs.

Inhibition of the Secretion of Cytokines

The activity of the products of the invention on the secretion of cytokines by human mononuclear cells was measured in vitro according to a method described by Konno S. et al. (1994) Eur. J. Pharmacol. 264: 265–268 and Endo H. et al. (1993) Int. Arch. Allergy Immunol. 101: 425–430 for the interleukins, and by Semmler J. et al. (1993) Int. J. Immunopharmac. 15: 409–413 and Verghese M. W. et al. (1995) J. Pharmacol. Exp. Ther. 272: 1313–1320 for TNFα.

Toxicity is evaluated in rats through per os administration. Administered in aqueous suspension in 1% methylcellulose, at the dose of 100 mg/kg/d, the products according to the invention showed no activity which can be linked to a toxic effect.

In particular, the absence of emesis-producing effects is observed.

These results demonstrate the anti-inflammatory and/or antiallergic activity of the products of the invention. Hence the products of the invention will be especially useful for the treatment or prevention of:

allergic pathologies, and in particular asthma and atopic dermatitis;

inflammatory pathologies, in particular those affecting the bronchus, but also rheumatoid arthritis and also inflammatory intestinal complaints (haemorrhagic rectocolitis and Crohn's disease); including, where it is present, an autoimmune component.

PHARMACEUTICAL FORMULATION PART

The products of the invention are administered in the form of compositions suited to the nature and extent of the complaint to be treated. The daily dosage in man is usually between 2 mg and 1 g of product, which can be taken in one or several doses. The compositions are prepared in forms which are compatible with the administration route envisaged, such as, for example, tablets, dragées, capsules, mouthwashes, aerosols, powders for inhalation, suppositories, gels or suspensions. These compositions are prepared by methods familiar to a person skilled in the art, and comprise from 0.5 to 60% by weight of active principle and 40 to 99.5% by weight of suitable pharmaceutical vehicle which is compatible with the active principle and the physical form of the composition envisaged. The composition and the preparation of tablets containing a compound of the invention are presented by way of example:

| | |
|---|---|
| Active substance of formula (I) | 1 to 75 mg |
| Lactose | 124 to 74 mg |
| Microcrystalline cellulose | 36 to 60 mg |
| Polyvinylpyrrolidone | 6 mg |
| Sodium carboxymethyl starch | 8 mg |
| Magnesium stearate | 1 mg |

Mix the active substance, lactose, microcrystalline cellulose and carboxymethyl starch. Wet and granulate using an aqueous or alcoholic solution of polyvinylpyrrolidone of appropriate concentration. Dry and calibrate the granulate. Homogeneously mix the magnesium stearate. Tablet on the basis of 200 g per tablet.

What is claimed is:

1. A compound of formula (III)

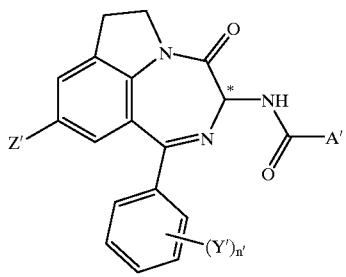

wherein:
Z' is hydroxymethyl, formyl, carboxylic acid in its free form, salified, esterified or amidated, hydroxymethyl whose hydroxyl group is esterified;
A' is aryl, a nitrogen-containing, 4- to 7-membered, unsaturated monocyclic group having carbon atoms and from 0 to 3 additional heteroatoms selected from the group consisting of nitrogen and sulphur, a sulphur-containing, 4- to 7-membered, unsaturated monocyclic group having carbon atoms and optionally from 0 to 3 additional heteroatoms selected from the group consisting of nitrogen and sulphur, or an unsaturated fused bicyclic group having carbon atoms and containing 1 heteroatom which is nitrogen or sulphur and optionally from 0 to 3 additional heteroatoms selected from the group consisting of nitrogen and sulphur, each optionally substituted with one to three groups independently chosen from halogen, lower alkyl, haloalkyl, lower alkoxy, hydroxyl, acetoxy, amino, t-butoxycarbonylamino, cycloalkylcarbonylamino or acetamido, the N-oxide or S-oxide forms;
Y' is hydroxyl or lower alkoxy;
n' is 0, 1 or 2;
as the racemic form thereof, or its isomers having a configuration which is determined by the carbon at the 3-position of the diazepinoindol 4-one ring, or its pharmacologically acceptable salts.

2. The compound according to claim 1, where Z' is chosen from the group consisting of hydroxymethyl; formyl; COOH; CONH$_2$, COOD where D is a lower alkyl, optionally hydroxylated; —CH$_2$—O—C(O)—E where E is a lower alkyl, an aryl, cycloalkyl, pyridyl.

3. The compound according to claim 1 or 2, where Y' is hydroxyl or methoxy.

4. The compound according to claim 1 or 2, where the phenyl is substituted at the para-position.

5. The compound according to 4, where the phenyl is substituted at the para-position with a hydroxyl.

6. The compound according to claim 1 or 2, where A' is pyridyl, optionally N-oxidized.

7. The compound according to claim 1 or 2, where the asymmetric carbon atom at the alpha-position with respect to the carbonyl of the diazepine ring has the absolute configuration (R).

8. The compound according to claim 3, where phenyl is substituted at the para-position.

9. The compound according to claim 8, where the phenyl is substituted at the para-position with hydroxyl.

10. The compound according to claim 3, where A' is pyridyl, optionally N-oxidized.

11. The compound according to claim 4, where A' is pyridyl, optionally N-oxidized.

12. The compound according to claim 8, where A' is pyridyl, optionally N-oxidized.

13. The compound according to claim 9, where A' is pyridyl, optionally N-oxidized.

14. The compound according to claim 3, where the asymmetric carbon atom at the alpha-position with respect to the carbonyl of the diazepine ring has the absolute configuration (R).

15. The compound according to claim 4, where the asymmetric carbon atom at the alpha-position with respect to the carbonyl of the diazepine ring has the absolute configuration (R).

16. The compound according to claim 8, where the asymmetric carbon atom at the alpha-position with respect to the carbonyl of the diazepine ring has the absolute configuration (R).

17. The compound according to claim 9, where the asymmetric carbon atom at the alpha-position with respect to the carbonyl of the diazepine ring has the absolute configuration (R).

18. The compound according to claim 10, where the asymmetric carbon atom at the alpha-position with respect to the carbonyl of the diazepine ring has the absolute configuration (R).

19. The compound according to claim 11, where the asymmetric carbon atom at the alpha-position with respect to the carbonyl of the diazepine ring has the absolute configuration (R).

20. The compound according to claim 12, where the asymmetric carbon atom at the alpha-position with respect to the carbonyl of the diazepine ring has the absolute configuration (R).

21. The compound according to claim 13, where the asymmetric carbon atom at the alpha-position with respect to the carbonyl of the diazepine ring has the absolute configuration (R).

22. A compound adoring to claim 1 selected from the group consisting of:

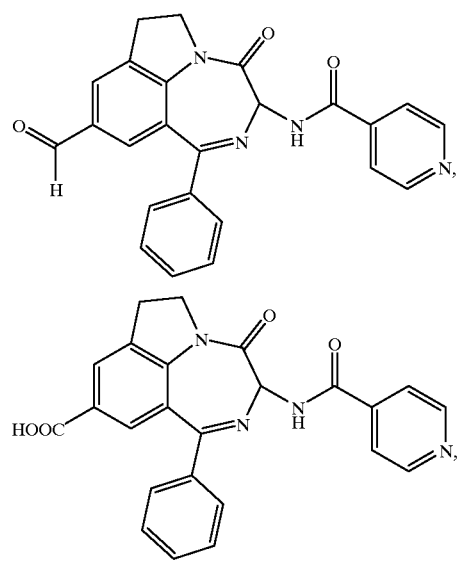

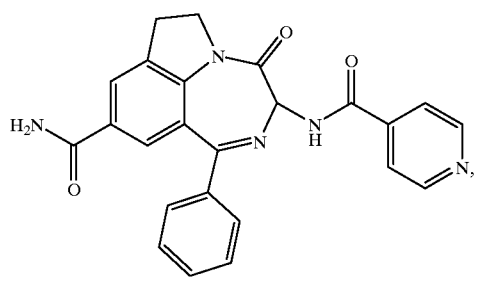
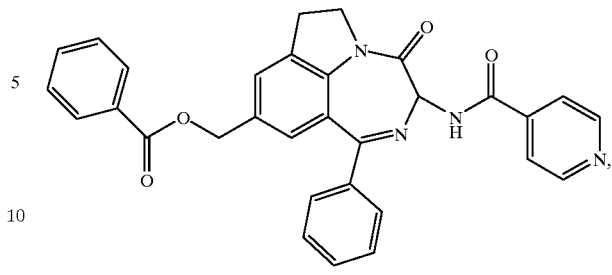
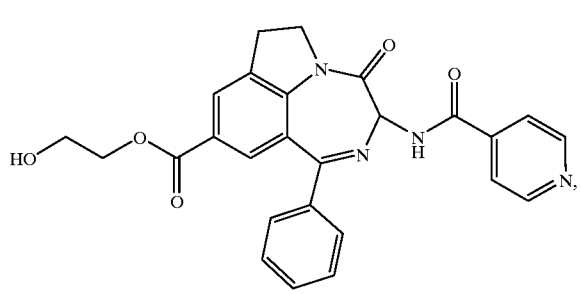
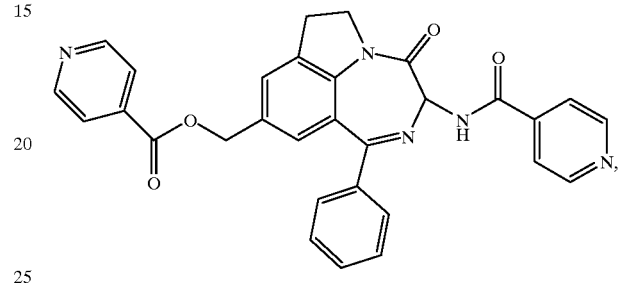
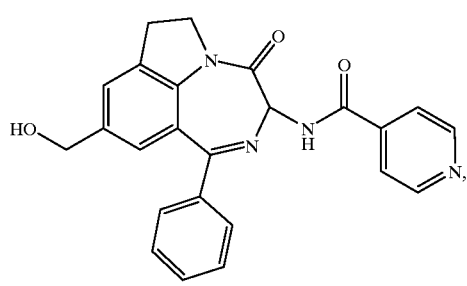
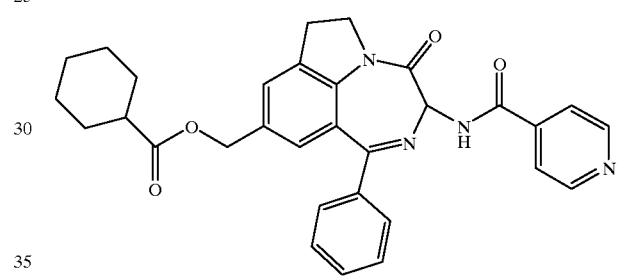
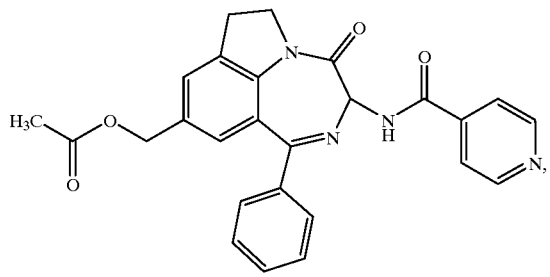
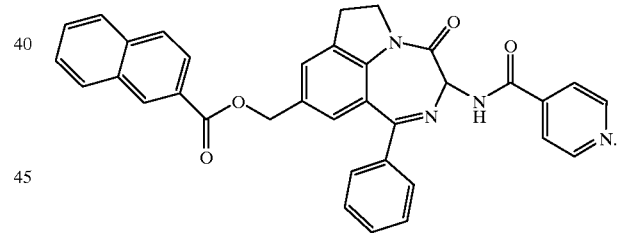
and
* * * * *

UNITED STATES PATENT AND TRADEMARK OFFICE
CERTIFICATE OF CORRECTION

PATENT NO. : 6,365,585 B1  
DATED : April 2, 2002  
INVENTOR(S) : Jacobelli et al.

Page 1 of 1

It is certified that error appears in the above-identified patent and that said Letters Patent is hereby corrected as shown below:

<u>Column 13,</u>
Line 60, insert -- the -- before "phenyl".

Signed and Sealed this

Seventeenth Day of September, 2002

Attest:

Attesting Officer

JAMES E. ROGAN
*Director of the United States Patent and Trademark Office*